US006760936B1

(12) United States Patent
Lloyd

(10) Patent No.: US 6,760,936 B1
(45) Date of Patent: Jul. 13, 2004

(54) METHOD AND MEANS FOR IMPROVING THE SLEEPING POSTURE OF A USER

(76) Inventor: Robert Guy Beechey Lloyd, 14 Graymount Gardens, Newtownabbey, County Antrim, BT36 7DY (GB)

( * ) Notice: Subject to any disclaimer, the term of this patent is extended or adjusted under 35 U.S.C. 154(b) by 0 days.

(21) Appl. No.: 10/018,512

(22) Filed: Apr. 5, 2002

(30) Foreign Application Priority Data

Jun. 15, 1999 (GB) ............................................ 9913719
Jun. 24, 1999 (GB) ............................................ 9914663

(51) Int. Cl.[7] .......................... A47G 9/00; A61G 7/075; A61F 5/01

(52) U.S. Cl. ................................ 5/650; 2/24; 128/882; 128/846

(58) Field of Search ..................... 5/648, 650; 128/845, 128/846, 882, 869; 2/24, 62

(56) References Cited

U.S. PATENT DOCUMENTS

| | | | | | |
|---|---|---|---|---|---|
| 2,552,177 | A | * | 5/1951 | Hurt | 2/24 |
| 2,805,420 | A | * | 9/1957 | Spellos | 5/648 |
| 4,177,806 | A | * | 12/1979 | Griffin | 5/648 |
| 4,484,361 | A | * | 11/1984 | Leighton et al. | 2/24 |
| 4,736,477 | A | * | 4/1988 | Moore | 5/648 |
| 4,879,765 | A | * | 11/1989 | Bailie et al. | 2/24 |
| 5,216,771 | A | * | 6/1993 | Hoff | 5/648 |
| 5,978,962 | A | * | 11/1999 | Hamowy | 2/24 |
| 6,145,508 | A | * | 11/2000 | Seip, Jr. | 128/845 |

* cited by examiner

*Primary Examiner*—Alexander Grosz
(74) *Attorney, Agent, or Firm*—Melvin I. Stoltz

(57) ABSTRACT

The sleeping posture of a user is improved by the use of a cotton cushion (10) which is attached to one of the legs of the user by means of an elasticated tubular bandage (11) and fits between the two knees of the user when the user's legs are located one on top of the other.

8 Claims, 2 Drawing Sheets

METHOD AND MEANS FOR IMPROVING THE SLEEPING POSTURE OF A USER

FIELD OF THE INVENTION

This invention relates to a method and means for improving the sleeping posture of a user.

BACKGROUND TO THE INVENTION

Poor sleeping posture creates restlessness, which results in undue stress and creates back pain.

Back pain is the single most common reason given by people taking days off work and is generally blamed on poor quality beds and incorrect sleeping posture.

In addition, back pain is particularly prevalent among geriatric patients in nursing homes where, in order to avoid the problems associated with sleeplessness, it is not uncommon for a patient to be given a "sleeping" pill every evening and a "wake-up" pill every morning.

It is accordingly an object of the present invention to provide a method for improving the sleeping posture of, for example, the elderly and infirm, the chronically sick, coma patients, pregnant women, those who suffer arthritis from their hips down, and those who suffer pain or discomfort as a result of old or recent sports injuries to their legs.

It is also an object of the present invention to provide means for improving the sleeping posture of a user.

A number of pillows and cushions have been proposed for this purpose and examples are shown in U.S. Pat. Nos. 4,177,806; 4,736,477; 4,889,109 and 5,418,991. Such pillows and cushions have a number of drawbacks and none have achieved common acceptance.

It is accordingly a more specific object of the present invention to provide an improved method and means for improving the sleeping posture of a user.

SUMMARY OF THE INVENTION

According to a first aspect of the present invention there is provided a method of improving the sleeping posture of a user, said method comprising the provision of a washable, air-pervious cushion to which is attached a tubular elasticated bandage for enabling the cushion to be attached releasably to a leg of the user, and the attachment of the cushion to the leg of the user by means of the tubular elasticated bandage so that the cushion fits between the two legs of the user, thereby facilitating the user sleeping in the semi-foetal position with his or her legs located one on top of the other.

The cushion is preferably attached to that leg of the user which, in the sleeping position, will be the lower leg of the user, the cushion being located adjacent the knee of said leg so that it fits between the user's knees.

According to a second aspect of the present invention there is provided means for improving the sleeping posture of a user, said means comprising a washable, air-pervious cushion to which is attached a tubular elasticated bandage for enabling the cushion to be attached releasably to a leg of a user, such that the cushion can be fitted between the two legs of the user, thereby facilitating the user sleeping in the semi-foetal position with his or her legs located one on top of the other.

The cushion preferably has a cotton or polyester and cotton cover and a filling which is either of cotton or lambswool.

DESCRIPTION OF THE PREFERRED EMBODIMENT

Figure 1:
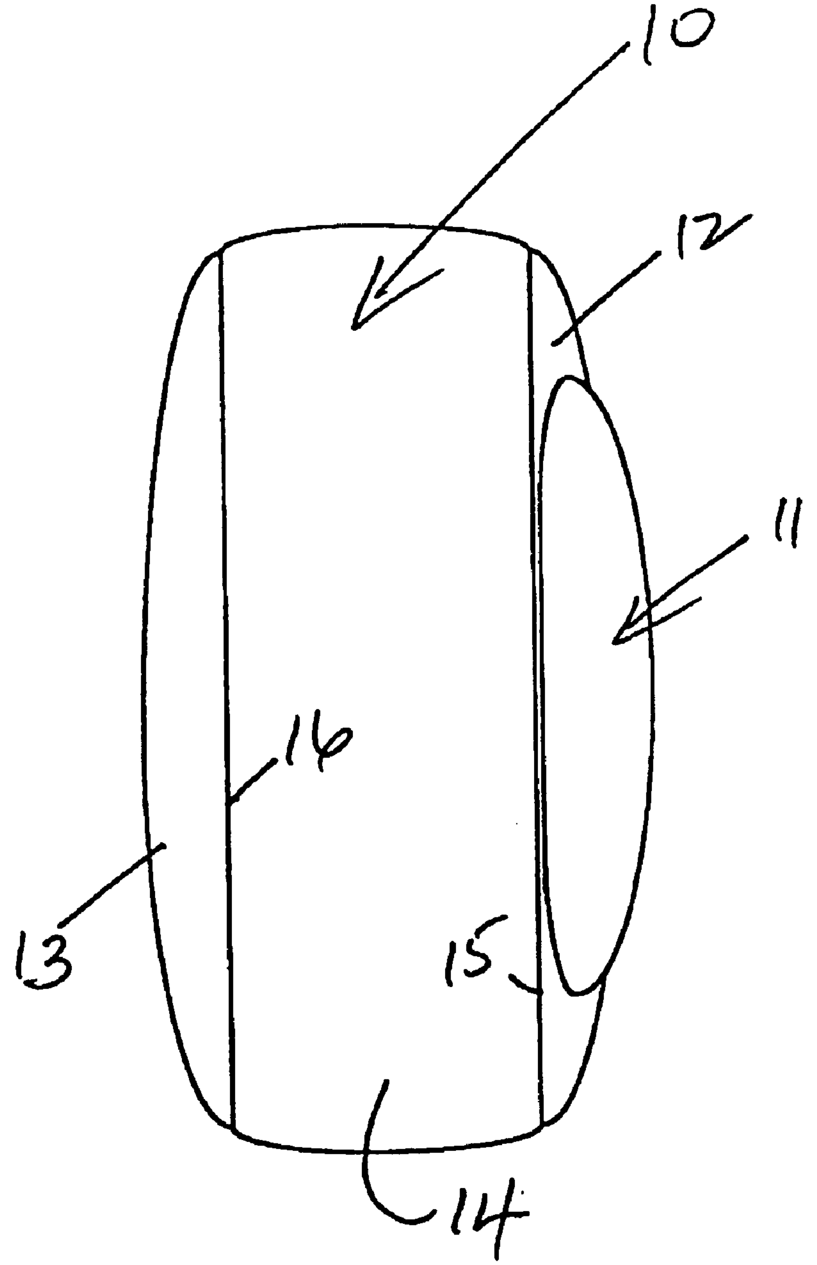
FIG. 1 is a side view of a device for improving sleeping posture.
Figure 2:
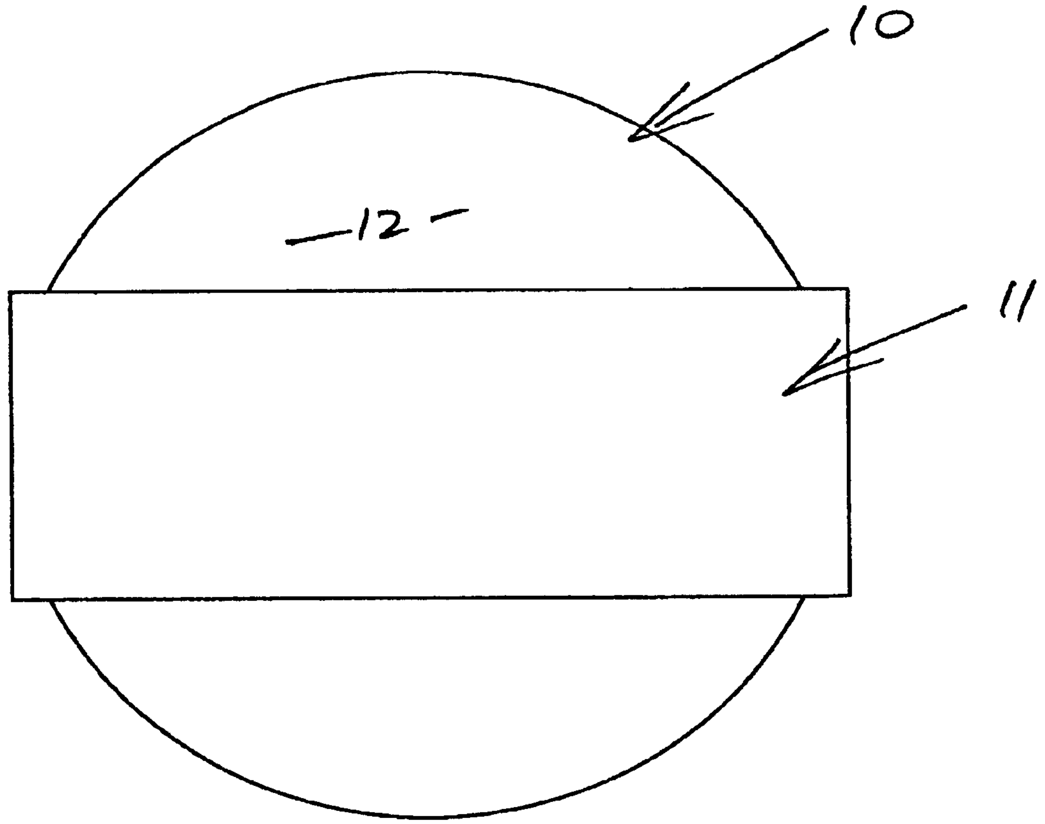
FIG. 2 is an underneath plan view of the device.

The device shown in the drawings is for fitment to a leg of a user in the vicinity of the knee of the user and will normally be attached to that leg of the user which is the lower leg when the user is sleeping on his or her "normal" side, i.e. the side on which he or she normally sleeps.

The device includes a cushion 10 and a tubular, elasticated bandage 11, such as a support bandage, which is stitched firmly to the cushion 10. The cushion 10 can be of circular form in plan view, as shown in the drawings, but may be of other configurations such as to enable it to provide a cushioning action between the knees of the user.

The size of the cushion 10 will depend on the size of the legs of the user and, for a circular cushion, the diameter may be from 150 to 300 mm and the thickness from 75 to 150 mm. The tubular, elasticated bandage 11 will have a diameter dependant on the size of the limbs of the user and a length substantially the same as the diameter of the cushion, i.e. from 150 to 300 mm.

As shown, the cushion 10 has a cover formed from three parts, i.e. circular parts 12 and 13 and a circumferential strip 14 which is sewn to the circumferences of the two circular parts 12 and 13 by lines of stitching 15 and 16. The tubular, elasticated bandage 11 is placed in contact with one 12 of the circular parts and is secured at each of its ends to the cushion 10 by lines of stitching which coincide with line of stitching 15 and extend for about a quarter of the circumference of each end of the bandage 11.

The cover of the cushion 10 is of pure white cotton or polyester and cotton, and may be of brushed white cotton. It has a filling which is of pure cotton quilt or of lambswool or of hollow fibre polyester. The stitching together of the parts 12, 13 and 14 of the cushion 10 is carried out using pure white cotton and the stitching of the elasticated bandage 11 to the cushion 10 is also carried out using pure white cotton.

The choice of materials is based on the need for softness, lack of chafing and durability of the device. Making the cushion 10 entirely of cotton, or with a cotton or polyester and cotton cover and a lambswool or hollow fibre polyester filling, makes it air-pervious and washable, i.e. it enables the cushion 10 to withstand at least thirty washes and enables it to be bleached regularly. The tubular, elasticated bandage 11 is made from materials which enable the bandage 11 to withstand the same treatment, i.e. either cotton or polyester.

If the filling is made from hollow fibre polyester, it has the advantage that it retains substantially no liquid so that, when the device requires washing, this can very rapidly be effected and the washed device dries out very quickly, ready for re-use.

This means that the device can be used in care homes and for geriatric patients, including those who are incontinent.

The device can readily be fitted in position by passing the foot through the tubular bandage 11 and then sliding the bandage 11 up the users leg until it the cushion 10 is in register with the inside of the knee. The cushion 10 will then be held resiliently in the required position while the user is sleeping and does not include any sharp edges or the like which could cause injuries to the user or restrict blood flow.

Use of the device enables the user to sleep in the semi-foetal position with his or her legs one on top of the other.

The spine of the user will thus not be subjected to the strains which would result from placing one leg in front of the other. The incidence of back pain will be reduced not only for the elderly but also for pregnant women and for those who have leg injuries or who suffer from arthritis from their hips down.

The device may also be used as a preventative measure by those who wish to ensure that they do not suffer from back, pains caused by an incorrect sleeping posture.

The cost of providing the device, and replacing it at regular intervals for the elderly or infirm, will be significantly less than the costs currently incurred in providing "sleeping" pills and "wake-up" pills. The long-term benefits of reducing the incidence of back pain in the working force will be immeasurable.

The device can be maintained in a hygienic condition and is environmentally friendly.

What is claimed is:

1. A method for improving the sleeping posture of a user, said method comprising the steps of:

A. proving a washable, air-pervious cushion comprising a major dimension ranging between about 150 mm and 300 mm and an overall thickness ranging between about 75 mm and 150 mm, and incorporating a single, tubular shaped, continuous, elastic bandage affixed thereto for enabling the cushion to be releasably attached to one leg of the user;

B. inserting one leg of the user between the cushion and the tubular, elastic bandage;

C. longitudinally advancing the cushion and bandage along the lower leg of the user; and D. placing the cushion on the inside edge of the leg of the user directly adjacent the knee, with the elastic bandage peripherally surrounding the knee, enabling the cushion to fit between the two legs of the user in juxtaposed, contacting relationship with the two knees of the user; thereby facilitating the user sleeping in the semi fetal position with his/her legs located one on top of the other.

2. A method as claimed in claim 1, in which the cushion (10) is attached to that leg of the user which, in the sleeping position, will he the lower leg of the user, the cushion (10) being located adjacent the knee of said leg so that it fits between the user's knees.

3. Means for improving the sleeping posture of a user, said means comprising:

A. a washable, air-pervious cushion incorporating
   a. a small, compact size dimensioned for cooperating with the knee area of the leg of a user comprising a major dimension ranging between about 150 mm and 300 mm and an overall thickness ranging between about 75 mm and 150 mm,
   b. a top cover, a bottom cover, and a side wall interconnected with the terminating edges of the top cover and bottom cover for forming the outer peripheral surface of the cushion and defining an interior zone therebetween, and
   c. soft, compressible, filling material inserted into said interior zone; and B. a single, continuous, elastic bandage securely affixed by stitching at each of its terminating edges to one of said covers, directly adjacent the interconnection of the cover to the side wall, thereby forming a generally tubular shaped elastic bandage for enabling the cushion to be releasably attached to the leg of the user;

Whereby the cushion is capable of being easily fitted between the two legs of the user and securely retained in position directly adjacent the knee by the single, tubular shaped, elastic bandage, facilitating the user sleeping in the semi-fetal position with his/her legs located one on top of the other.

4. Posture improving means as claimed in claim 3, in which the parts forming the cushion are defined as comprising at least one material selected from the group consisting of cotton, polyester, brushed white cotton, and combinations thereof.

5. Posture improving means as claimed in claim 4, in which the cover is made of a plurality of parts sewn together using cotton and in which the tubular elasticated bandage is sewn to the cover using cotton.

6. The posture improving means defined in claim 3, wherein the filling material is further defined as comprising at least one selected from the group consisting of cotton, lamb's wool, hollow fiber polyester, and combination thereof.

7. The posture improving means defined in claims 3, wherein the elastic bandage is further defined as being washable and sewn to the cover by employing thread material selected from the group consisting of cotton, polyester, and cotton-polyester combinations.

8. The posture improving means defined in claim 3, wherein said cushion further comprises a substantially circular shape.

* * * * *